(12) United States Patent
Maurel (10) Patent No.: US 11,789,000 B2
(45) Date of Patent: Oct. 17, 2023

(54) ASPIRATING DETECTION SYSTEM AND METHOD

(71) Applicant: Carrier Corporation, Palm Beach Gardens, FL (US)

(72) Inventor: Ricard Burriel Maurel, Barcelona (ES)

(73) Assignee: CARRIER CORPORATION, Palm Beach Gardens, FL (US)

( * ) Notice: Subject to any disclaimer, the term of this patent is extended or adjusted under 35 U.S.C. 154(b) by 229 days.

(21) Appl. No.: 17/126,327

(22) Filed: Dec. 18, 2020

(65) Prior Publication Data

US 2021/0364486 A1 Nov. 25, 2021

(30) Foreign Application Priority Data

May 22, 2020 (EP) .................................... 20382435

(51) Int. Cl.
*G01N 33/00* (2006.01)
*G08B 17/10* (2006.01)
(Continued)

(52) U.S. Cl.
CPC ..... *G01N 33/0062* (2013.01); *G01N 33/0011* (2013.01); *G08B 17/10* (2013.01); *G01N 1/2273* (2013.01); *G01N 1/24* (2013.01)

(58) Field of Classification Search
CPC ........... G01N 33/0011; G01N 33/0062; G01N 1/2273; G01N 1/24; G08B 17/10; G08B 29/18
See application file for complete search history.

(56) References Cited

U.S. PATENT DOCUMENTS

| 9,940,806 B2 * | 4/2018 | Al-Farra | G08B 29/185 |
| 2007/0008157 A1 * | 1/2007 | Siemens | G08B 17/10 340/628 |

(Continued)

FOREIGN PATENT DOCUMENTS

| JP | 2016015028 A | * | 1/2016 |
| JP | 2016015028 A | | 1/2016 |

(Continued)

OTHER PUBLICATIONS

Machine Translation of RU-2580816-C1 (Year: 2016).*
Extended European Search Report for International Application No. 20382435.4 dated Nov. 16, 2020, 29 pages.

*Primary Examiner* — Nathaniel J Kolb
(74) *Attorney, Agent, or Firm* — CANTOR COLBURN LLP (57) ABSTRACT

An aspirating detection system, a heat-detection device for an aspirating detection system, and a method of determining that a temperature in a monitored environment has exceed a predetermined threshold are provided. An aspirating detection system for monitoring an environment, the system including: an aspirating detector for aspirating and detecting smoke in a sample of air; a sampling pipe or providing a sample of air to the aspirating detector, the sampling pipe at least partially exposed to the monitored environment; and a heat-detection device exposed to the monitored environment and arranged to emit an airborne substance into the sampling pipe when the temperature of the monitored environment exceeds a predetermined threshold; the aspirating detector is arranged to detect the airborne substance and thereby detect that the temperature of the monitored environment exceeds the predetermined threshold.

16 Claims, 1 Drawing Sheet

(51) Int. Cl.
  *G01N 1/24*  (2006.01)
  *G01N 1/22*  (2006.01)

(56) References Cited

U.S. PATENT DOCUMENTS

2012/0285710 A1    11/2012  Umehara et al.
2016/0314669 A1*   10/2016  Al-Farra ................ G08B 17/10

FOREIGN PATENT DOCUMENTS

RU           2580816  C1 *  4/2016
WO         2014082122 A2    6/2014

* cited by examiner

ASPIRATING DETECTION SYSTEM AND METHOD

FOREIGN PRIORITY

This application claims priority to European Patent Application No. 20382435.4 filed May 22, 2020, the entire contents of which is incorporated herein by reference.

TECHNICAL FIELD

The present invention relates to an aspirating detection system, a heat-detection device for an aspirating detection system, and a method of determining that a temperature in a monitored environment has exceeded a predetermined threshold.

BACKGROUND

Aspirating detection systems are generally used to monitor multiple buildings or rooms for airborne particulates or gasses using a single detection system. In a conventional aspiration detection system, air from the one or more buildings or rooms to be monitored is aspirated through a network of one or more pipes to a central aspirating detection unit. The central detection unit then analyses a sample of the aspirated air to detect the airborne particulates or gasses. For example, aspirating detection systems may be configured to detect smoke which may indicate a fire, to detect natural gas which may indicate a gas leak, or to detect carbon monoxide for safety purposes. They may also be implemented for other detection purposes.

There are many advantages in using aspirating detection systems over conventional point detectors. For example, using a network of one or more pipes, which require no electrical power, to cover a large area rather than using an array of multiple point detectors may avoid the need for electrical wiring to be installed or modified in the building or room to be covered. This is particularly relevant for example in buildings of historical importance, where it is desired to preserve the integrity of the building, or for spaces where vandalism of the system's electronics may need to be prevented, such as prisons or public spaces. Additionally or alternatively, this is also particularly relevant for environments in which the introduction of electricity could be hazardous due to the atmosphere, for example in a battery factory, chemical production plant, or otherwise. Further, the implementation of one or more central detection units to detect one or more substances obviates the need for multiple point detectors installed over the area to be monitored. As such the cost of a higher sensitivity detector may be offset by the fact that only a single central detection unit may be necessary to detect a desired substance, rather than a multiplicity of point detectors.

In rooms or buildings where there is a naturally high prevalence of smoke, such as industrial warehouses, kitchens, factories or otherwise, aspirating detection systems may suffer false alarms and it may be appropriate to implement a separate heat-detection system where heat is detected as a condition indicative of a fire, rather than smoke. The heat-detection system may operate alongside or in place of the aspirating detection system. This may avoid nuisance or false alarms generated upon the detection of smoke from a known source by an aspirating detection system. In examples where the heat-detection system operates alongside the aspirating detection system, the aspirating detection system may be configured to be less sensitive to smoke, or configured to not detect smoke and instead to detect other particulates or gasses. This may avoid nuisance alarms or the undesirable detection of smoke that is not indicative of a safety-critical event like a fire.

One such conventional heat-detection system which may be implemented alongside an aspirating detection system for this purpose is a linear heat-detection system. Linear heat-detection systems generally comprise two parallel wires, isolated from one another by a casing formed of polymeric material. The polymeric casing is configured to melt at a chosen temperature which is to be detected, and upon being exposed to heat of said temperature, melts. The two wires, previously isolated from one another, come into contact. Upon contact, an electric circuit is completed and/or short-circuited and the generated current or resistance is used to signal the detection of the target temperature.

Linear heat-detection systems are independent from any aspirating detection system they may run parallel to, and accordingly may generally be installed separately. This may damage buildings or rooms during their installation. Further the entire linear heat-detection system, or at least the relevant wiring, covering a large area, may need to be replaced each time the polymeric wire casing is melted. The linear heat-detection system, being a separate system to an aspirating detection system, may also increase costs associated with installing required fire detection and prevention equipment. Additionally, linear heat-detection systems require electricity to function which may be unsuitable for the monitoring of some environments.

It is desirable to provide improvements in environmental monitoring systems such as aspirating detection systems, which may provide improved safety and fire monitoring services.

SUMMARY

Viewed from a first aspect the invention provides an aspirating detection system for monitoring an environment, the system comprising: an aspirating detector for aspirating and detecting smoke in a sample of air, a sampling pipe for providing a sample of air to the aspirating detector, the sampling pipe at least partially exposed to the monitored environment, and a heat-detection device exposed to the monitored environment and arranged to emit an airborne substance into the sampling pipe when the temperature of the monitored environment exceeds a predetermined threshold, wherein the aspirating detector is arranged to detect the airborne substance and thereby detect that the temperature of the monitored environment exceeds the predetermined threshold.

By using an aspirating detection system to detect heat rather than merely detecting smoke, it is possible to increase the functionality of the aspirating detection system e.g. to detect smokeless heat. This may allow for the detection of overheating events which may be indicative of e.g. damage to a monitored environment or its contents, and/or events which may be a precursor to such damage and/or a fire event.

By detecting the airborne substance, the aspirating detection system is capable of detecting heat exceeding the predetermined threshold, as the emission of the airborne substance from the heat-detection device occurs only when the heat-detection device is exposed to such conditions present in the monitored environment.

Since the system comprises a heat-detection device, the aspirating detection system may be configured to detect the airborne substance rather than (or as well as) smoke. Smoke can be a result of for example a fire but also processes such as cooking or manufacturing that otherwise cause nuisance alarms. The heat-detection device may therefore indicate a fire by the emission of the airborne substance, rather than a generic smoke produced by a known source, and may therefore help reduce instances of false alarms.

Additionally, the heat-detection device may emit the airborne substance in response to heat not necessarily from a fire source, but to any heat of the monitored environment which exceeds the predetermined threshold. By releasing the airborne substance when no airborne substance would otherwise be released, the heat-detection device may indicate heat conditions which suggest damage or future damage to, for example, electronic or machine components. The temperature may be a precursor to a fire. Preventative and/or failsafe measures may then be implemented such that damage to electronic or machine equipment, or otherwise, may be reduced, avoided and/or minimised.

Further, the heat-detection device may require no electronic components or wiring. That is, the heat-detection device may be a passive device. The heat-detection device may be suitable for installation in the aspirating detection system without electronic communication and/or electrical connection. As such, damage to buildings and/or infrastructure may be avoided as no electronic wiring is necessary to provide adequate heat-detection. No wiring or electricity is needed for the aspirating detection system other than that required for the aspirating detector, which may (or may not) be located remotely from the environment to be monitored. As will be appreciated, the sampling pipe may be a plastic pipe or otherwise and may not require electronics. Accordingly no supplementary electronic or wires for electronic communication and/or electrical connection are required in the monitored environment. Thus, the aspirating detection system may be operable to detect heat in the monitored environment without requiring electricity in the monitored environment. It may therefore be employed for detecting heat in environments that cannot have electricity introduced therein, or in which the introduction of electricity is a hazard.

The aspirating detection system may be configured to raise an alarm in response to detecting that the temperature of the monitored environment exceeds the predetermined threshold. The alarm may be a visual alarm and/or an aural alarm. The aural alarm may be generated by a siren, a speaker, a bell or the like. The visual alarm may be generated by a stroboscopic light, an LED, or a message on a display panel. The alarm may be an email, SMS message or the like sent to a communication device such as a smartphone. The aspirating detection system may release a suppressant into the monitored environment in order to reduce the temperature therein. Alternatively, the aspirating detection system may not release a suppressant into the monitored environment in response to detecting that the temperature therein exceeds the predetermined threshold, and therefore the detection of heat (rather than e.g. of fire per se) may provide advanced warning of deteriorating conditions, but may not immediately require safety critical actions, such as the discharge of suppressant.

The aspirating detection system may be operable to cool the monitored environment in response to detecting that the temperature of the monitored environment exceeds the predetermined threshold. The cooling may be performed by a sprinkler system. The sprinkler system may be configured to spray water or any suitable suppressant in the monitored environment. The cooling may be performed by an air conditioning unit. The cooling may be performed by a cryogenic gas cooling system. The aspirating detection system may be arranged to discharge a suppressant into the monitored environment in response to detecting that the temperature of the monitored environment exceeds the predetermined threshold. The aspirating detection system may comprise a fire extinguishing device configured to discharge the suppressant. The suppressant may be any known fire extinguishing suppressant.

The aspirating detection system may be configured so that in response to detecting that the temperature of the monitored environment exceeds the predetermined threshold, it compares the predetermined threshold to a temperature threshold, and the system may select a response based upon that comparison. For example, if the predetermined threshold is greater than the temperature threshold, the aspirating detection system may respond differently to how it would respond if the predetermined threshold is less than the temperature threshold. The system may respond using any and all of the functions described herein. The system may be configurable by a user to respond as needed.

The aspirating detection system may comprise a fire panel and/or command module. The fire panel and/or command module may be configured to coordinate the response of the aspirating detection system to the detection that the temperature of the monitored environment exceeds the predetermined threshold. The fire panel and/or command module may be configured to raise an alarm in response to detecting that the temperature of the monitored environment exceeds the predetermined threshold. The fire panel and/or command module may be configured to generate a signal to cool the monitored environment in response to detecting that the temperature of the monitored environment exceeds the predetermined threshold. The fire panel and/or command module may be configured to generate a signal to discharge a suppressant into the monitored environment in response to detecting that the temperature of the monitored environment exceeds the predetermined threshold. The fire panel and/or command module may be configured to send a notification such as an email or a text message or the like in response to detecting that the temperature of the monitored environment exceeds the predetermined threshold. The notification may provide the predetermined threshold and indicate that the temperature exceeds that.

The fire panel and/or command module may comprise a processor. The fire panel and/or command module may be in electronic communication with the aspirating detector, and may be arranged to receive a signal from the aspirating detector e.g. that a temperature exceeding the predetermined threshold has been detected by detection of the airborne substance. The fire panel and/or command module may be programmable to define a response of the aspirating detection system upon detecting that the temperature of the monitored environment exceeds the predetermined threshold.

The aspirating detector may be for aspirating a sample of air from the monitored environment via the sampling pipe, and may be for detecting smoke in the aspirated sample. Thus, the aspirating detector may be fluidly connected to the sampling pipe for receiving a flow of fluid therefrom e.g. for receiving an airflow therefrom. Thus, the sampling pipe may supply a flow of fluid e.g. air to the aspirating detector during use.

The aspirating detector may detect the airborne substance using an optical sensing device. The aspirating detector may be a nephelometer. The aspirating detector may comprise a laser head. The laser head may be a high sensitivity laser head. The aspirating detector may use any suitable means for detecting the airborne substance.

The aspirating detector may be configured to detect a plurality of gasses, airborne substances, particulates and the like. The aspirating detector may be configured to detect smoke and the airborne substance. The aspirating detector may be operable to distinguish between a plurality of airborne substances e.g. between smoke and the airborne substance emitted from the heat-detection device.

The aspirating detector may be configured to only detect the airborne substance. The aspirating detector may therefore not detect other substances and may only react to the temperature in the monitored environment exceeding the predetermined threshold.

The system may include an aspirating device for drawing a sample of air into the aspirating detector through the sampling pipe. For example, the aspirating device may be a pump, a fan, a compressor, or any suitable means for drawing a sample of fluid such as air into the system, and into the aspirating detector from the sampling pipe. The aspirating device may be part of the aspirating detector, or may be separate from the aspirating detector.

The sampling pipe may be at least partially within the monitored environment. The sampling pipe may thereby be exposed to the monitored environment and to conditions within the monitored environment. Thus, the sampling pipe may be exposed to temperature increases in the monitored environment. At least a portion of the sampling pipe may be arranged to be in thermal equilibrium with the monitored environment. The system may comprise a plurality of sampling pipes disposed throughout the monitored environment, and the plurality of pipes may be connected together and/or connected to the aspirating detector.

The sampling pipe may be any suitable size and may have any suitable diameter. The sampling pipe may have a diameter of 20 mm to 50 mm. The sampling pipe may have a diameter of 20 mm to 40 mm. The sampling pipe may have a diameter of 20 mm to 30 mm.

The monitored environment may comprise one or more buildings, rooms and/or apparatus to be monitored by the aspirating detection system.

The heat-detection device may be within the monitored environment and thereby exposed to conditions within the monitored environment. The heat detection device may therefore be heated in the event that the temperature in monitored environment increases. The heat-detection device may be arranged to be in thermal equilibrium with the monitored environment.

The heat-detection device may be installed on the sampling pipe. The heat-detection device may be installed in the sampling pipe. The heat-detection device may be mechanically coupled to the sampling pipe, and may be mechanically coupled by any suitable means. The system may include a mechanical coupling for coupling the heat-detection device to the sampling pipe. The mechanical coupling may comprise e.g. a screw, a clamp, a slot or any suitable mechanism.

The heat-detection device may be arranged to seal an opening in the sampling pipe to the monitored environment. The heat-detection device may thereby prevent fluid communication between the interior of the sampling pipe and the monitored environment, at least via the opening in the pipe at that location within the monitored environment. The heat-detection device may therefore prevent ingress into the sampling pipe from the monitored environment of smoke, particulates, or other substances that could be detected by the aspirating detector but which do not warrant an alarm. For example, if the monitored environment comprises a kitchen, a garage, and/or another environment in which smoke or the like is typically expected, the heat-detection device may function to prevent false alarms e.g. by preventing ingress of those into the sampling pipe. The heat-detection device may adhere to the sampling pipe. In doing so the heat-detection device may be operable to seal the opening in the sampling pipe. The heat-detection device and/or the sampling pipe may comprise a seal arranged to seal the heat-detection device in the opening of the sampling pipe.

The system may comprise a plurality of heat-detection devices and the interior of the pipe may be entirely sealed (at least from the monitored environment) by that plurality of heat-detection devices. The aspirating detection system may therefore be configured to function as only a heat-detection system.

Alternatively, the heat-detection device(s) may seal the sampling pipe only in a particular region of the monitored environment. For example, if the system is arranged to monitor a plurality of locations (e.g. including a kitchen and a library), the sampling pipe may be sealed by the heat-detection device(s) in one location (e.g. in the kitchen) to reduce the chance of false alarms from an environment where smoke or the like is expected, but may comprise openings in another location (e.g. in the library) for aspirating air and thereby detecting smoke e.g. in line with usual practices for an aspirating detection system. The aspirating system may be configured to operate as both a typical aspirating system for detecting e.g. smoke, and as a heat-detection system for detecting heat.

The heat-detection device may be a substance. For example, the heat-detection device could be a heat-responsive material and/or thermal paste. It may be applied to the sampling pipe e.g. in an interior of the sampling tube. Upon exposure to a temperature exceeding the predetermined threshold, the substance may undergo a reaction and/or phase change which results in the emission or discharge of the airborne substance.

The heat-detection device may have any suitable size e.g. for containing sufficient material that the aspirating detector can detect its discharge. The heat-detection device may be sized such that it may be installed in or on the sampling pipe. The heat-detection device may be installed externally to the sampling pipe, or may be installed internally. The heat-detection device may be installed on an extension of the sampling pipe e.g. on or in a dedicated portion of the sampling pipe.

The heat-detection device may be less than or equal to 20 mm in width and/or diameter. The heat-detection device may be less than or equal to 30 mm in width and/or diameter. The heat-detection device may be less than or equal to 50 mm in width and/or diameter. The heat-detection device may be less than or equal to 20 mm in height. The heat-detection device may be less than or equal to 30 mm in height. The heat-detection device may be less than or equal to 40 mm in height. The heat-detection device may be less than or equal to 50 mm in height.

The sampling pipe may be a network of sampling pipes. The sampling pipe may be a first sampling pipe, the first sampling pipe connected to a second sampling pipe. The sampling pipe may be an assembly of a plurality of pipes. The pipes may connect to each other, and/or may connect to the aspirating detector. Each pipe may be arranged so as to supply fluid therefrom to the aspirating detector.

The heat-detection device may be installed in a juncture of the network of pipes. The heat-detection device may be installed wherever is necessary within the network of pipes.

The airborne substance may be at least one of an aerosol or a target gas. The airborne substance may be paraffin smoke. The airborne substance may generally be a gas and/or substance which is not generally prevalent in the monitored environment. As such the detection of generally prevalent substances and/or compounds in the monitored environment causing nuisance alarms may be avoided. Generally prevalent gases may include, but are not limited to, oxygen, nitrogen, carbon dioxide, carbon monoxide, and methane. Generally prevalent aerosols may include smokes which are the combustion products of known fire sources within the location and/or vicinity of the heat capsule.

The combustion of various products may produce distinguishable smokes and/or substances. The airborne substance may be distinguishable from the generally prevalent gas and/or substance. The airborne substance may be detectable by the aspirating detector due to the airborne substance having a recognisably different signal and/or signature to that of generally prevalent gases and/or substances. The airborne substance may a substance capable of being aspirated by the aspirating detector. The aspirating detector may be operable to distinguish between a plurality of airborne substances.

The airborne substance may be generated as the result of a phase transition and/or a chemical reaction. For example, the heat-detection device may comprise and/or contain material in a liquid or solid form. When the heat-detection device is exposed to temperatures which exceed the predetermined threshold, the material may transition into a gaseous phase such that it may be aspirated by the aspirating heat detector. Similarly, the material may emit the airborne substance as an aerosol and any airborne particulates. For example, the material may be a substance which combusts at temperatures exceeding the predetermined threshold. The airborne substance may be product of combustion, explosion and/or pyrolysis, for example from a material that combusts, explodes or undergoes pyrolysis when exposed to the monitored environment at a temperature exceeding the predetermined threshold.

The monitored environment may comprise a first volume and a second volume, wherein the sampling pipe is disposed at least partially in the first volume and at least partially in the second volume, wherein the heat-detection device is disposed in the first volume, and wherein the sampling pipe comprises an opening into the second volume for aspirating air from the second volume.

The second volume may be separate or substantially separate from the first volume. The first volume may have a distinct or substantially distinct atmosphere to the second volume. For example, the first volume may be one in which smoke or the like is typically expected (e.g. a kitchen), and the second volume may be one in which smoke is not typically expected (e.g. a library). The use of the heat-detection device as described herein may therefore enable the system to monitor different types of environment simultaneously. The system may simultaneously monitor the first volume for an increase in temperature exceeding the predetermined threshold, and may monitor the second volume for smoke therein.

It will be appreciated that although the same pipe may be partially disposed in the two volumes, the system may include a second sampling pipe for monitoring the second volume. The sampling pipe may therefore be a first sampling pipe and may be exposed at least partially to the first volume. The second sampling pipe may be exposed at least partially to the second volume.

As will be appreciated, the first volume may refer to a building, room and/or apparatus present in the monitored environment. The second volume may refer to a building, room and/or apparatus present in the monitored environment.

The aspirating detection system may be operable to monitor a plurality of volumes. The monitored environment may comprise a plurality of volumes. Each volume may be substantially separated (or distinct) from the others. The sampling pipe may be at least partially exposed to each volume. The aspirating detection system may comprise a plurality of sampling pipes and one or more sampling pipes may be at least partially exposed to each volume. Thus, each volume may be served by at least one sampling pipe. Each pipe may have one or more heat-detection devices installed. One or more of the plurality of sampling pipes may not have a heat-detection device installed. Thus the aspirating detection system may be operable to simultaneously monitor a plurality of volumes for heat exceeding a predetermined threshold and a plurality of volumes for smoke therein.

The monitored environment may be the plenum of an apparatus. The first and/or second volume may be the plenum of an apparatus. The apparatus may be machinery. The apparatus may be an electrical apparatus. The apparatus may include, for example, a computer server. The plenum may be an empty space provided for cooling purposes and/or for housing various components. The plenum may be in fluid communication with the sampling pipe directly. The plenum may be in fluid communication with the sampling pipe indirectly, for example via a capillary tube e.g. for drawing fluid from the plenum into the sampling pipe.

By monitoring the apparatus including machinery and electrical apparatus, such devices may be monitored for overheating. Appropriate action may be taken to then preserve the condition of the apparatus or perform maintenance on the apparatus, for example. Such overheating events may be a precursor to fire events, or may just be likely to cause damage to the apparatus. Accordingly the aspirating detection system may detect if a monitored environment of an apparatus exceeds a given temperature.

The heat-detection device may be a first heat-detection device and the airborne substance may be a first airborne substance. The system may further comprise a second heat-detection device arranged to emit a second airborne substance when the temperature of the monitored environment exceeds a second predetermined threshold, wherein the aspirating detector is operable to detect the second airborne substance.

By providing a first heat-detection device and a second heat-detection device, each emitting a first and second airborne substance respectively when the temperature exceeds a predetermined threshold, the aspirating detection system may monitor multiple locations within the environment, and may detect when the temperature of the monitored environment at multiple locations exceeds the predetermined threshold. The first heat-detection device may be within the first volume and the second heat-detection device may be within the second volume.

Further, the first airborne substance may be different to the second airborne substance. The aspirating detector may be operable to distinguish between the first and second airborne substance. The system may therefore identify which of the first and second heat-detection device(s) was compromised. That is, which of the first and second heat-detection devices emitted its airborne substance upon being exposed to a temperature exceeding the predetermined threshold. An alarm may be raised, or further information deduced or action taken, based on which of the airborne substances was detected.

The first airborne substance and the second airborne substance may be different and the first and second heat-detection devices may be arranged to emit the respective airborne substances when exposed to respective environments at the first and second predetermined thresholds. The aspirating detector may be configured to distinguish between the first airborne substance and the second airborne substance and the aspirating detector may therefore be operable to distinguish which heat-detection device has been activated, and hence which predetermined threshold of temperature has been reached.

The second heat-detection device may be arranged to emit the second airborne substance when the temperature of the monitored environment exceeds a second predetermined threshold. The first heat-detection device may be arranged in the first volume and the second heat-detection device may be arranged in the second volume. The system may therefore be operable to determine which volume has a temperature in excess of the corresponding predetermined threshold. An alarm indicating heat-detection in the relevant volume may then be raised or any other suitable action may be taken. The aspirating detection system may comprise a plurality of heat-detection device, each with respective airborne substances and arranged to discharge those airborne substances when exposed to environments is excess of respective predetermined thresholds.

Although the first and second predetermined thresholds may be the same, they may also be different. The first and second heat-detection devices may be within the same monitored environment e.g. in the same volume, and may be configured to emit their respective airborne substances when the temperature of the environment is at different predetermined thresholds. For example, if the first predetermined threshold is lower than the second predetermined threshold, the aspirating detector may detect a progression of increasing temperatures within the monitored environment by initially detecting the first airborne substance, then detecting the second airborne substance. The system may be therefore be operable to monitor the severity of temperature increases in a monitored environment. The system may be configured to e.g. send a notification upon detection of the first predetermined threshold, then cool the environment upon detection of the second predetermined threshold. The aspirating detection system may therefore provide a type of early-warning system.

Any suitable combination of heat-detection device with respective predetermined thresholds may be used in any suitable configuration of sampling pipes. Each heat-detection device may be associated with a known location or volume, and a known predetermined threshold. The aspirating detection system may therefore provide increased functionality.

By being able to distinguish different temperatures in different volumes, the aspirating detection system may be able to provide a bespoke aspiration detection system. The combination of multiple heat-detection devices via the first and second heat-detection device within a single aspiration detection may negate the need for multiple linear heat-detection systems to be installed.

The aspirating detection system may be a pre-existing and/or a preinstalled aspirating detection system. The heat-detection device may be retrofitted to the aspirating detection system. By retrofitting the aspirating detection system with the heat-detection device, existing aspirating detection systems may be repurposed for detecting heat exceeding a predetermined threshold via the airborne substance, the airborne substance emitted from the heat-detection device when exposed to temperatures exceeding the predetermined threshold. Retrofitting aspirating detection systems may save costs, as conventional linear heat detectors need not be installed alongside and/or in place of existing aspirating detection systems.

The heat-detection device may contain or encapsulate the airborne substance, or a material that will emit or transition into the airborne substance at a relevant temperature e.g. when the monitored environment exceeds the predetermined threshold.

The heat-detection device may be a heat-detection capsule comprising a portion arranged to structurally fail when the temperature of the monitored environment exceeds the predetermined threshold and thereby release the airborne substance. The portion may therefore open the capsule when the temperature of the monitored environment reaches the predetermined threshold.

The portion may be a heat sensitive lid or closure, and may melt or degrade upon exposure to a sufficient temperature. The portion may be arranged to rupture when exposed to pressure from within the heat-detection capsule, for example caused by a phase transition, combustion, pyrolysis, or explosion of material within the capsule. The heat-detection capsule may contain the airborne substance and/or may contain material that emits and/or discharges the airborne substance (e.g. by phase transition, combustion, pyrolysis, and/or explosion) when exposed to an environment at a temperature exceeding the predetermined threshold.

Temperatures which cause the emission of the airborne substance may be configured as required to meet the demands of the aspirating detection system. However, appropriate temperatures for the predetermined threshold may be 40° C. or more, 45° C. or more, 50° C. or more, 55° C. or more, 60° C. or more, 65° C. or more, 70° C. or more, 80° C. or more, 90° C. or more, 100° C. or more, 110° C. or more, 120° C. or more, 130° C. or more, 140° C. or more, 150° C. or more, 160° C. or more, 170° C. or more, 180° C. or more, 190° C. or more, or 200° C. or more.

The predetermined threshold may be 5° C., 10° C., 15° C. or 20° C. above the temperature at which the heat detecting device is arranged to emit the airborne substance. This may account for configurations where the heat-detection device is not necessarily at the temperature of the monitored environment. There will be an efficiency of less than 1 for heat transfer between the monitored environment and the heat-detection device. For example, airflows from the aspirating detector or otherwise in the monitored environment may have cooling effects on the heat-detection device. The heat-detection device can be configured as required to emit the airborne substance.

The portion, which may be a heat sensitive lid or closure, may enclose the airborne substance, or material emitting the airborne substance, when in combination with a casing. The airborne substance, or corresponding material, may be encapsulated and/or enclosed in an enclosure defined by the heat sensitive portion and the casing.

The portion may be configured to melt when exposed to temperatures exceeding the predetermined threshold. The portion may be formed of a material with a melting point equal to the predetermined threshold, or less than the predetermined threshold. The material may be a polycarbonate material. The material may be a polymeric plastic. The material may be chosen such that it melts when exposed to an environment at a temperature exceeding the predetermined threshold.

The casing may be formed of a heat resistant material. The casing may be formed of polycarbonate acrylonitrile butadiene styrene (PC-ABS). The casing may be formed of a heat stable material. The casing may maintain its structural integrity when exposed to temperatures exceeding the predetermined threshold.

The heat-detection device may be a heat-detection capsule. The heat-detection capsule may comprise a casing, and the portion may be arranged to structurally fail when the temperature of the monitored environment exceeds the predetermined threshold and thereby release the airborne substance, the portion and the casing defining an enclosure containing the airborne substance.

By providing a heat-detection capsule which releases the airborne substance, the aspirating detection system may be able to detect when the monitored environment is at a temperature exceeding the predetermined threshold. Accordingly the aspirating detection system may be able to detect heat due to the provision of the heat-detection capsule.

Additionally, as the heat-detection capsule requires no electronic components or wiring, the heat-detection capsule may be suitable for installation without electronic communication and/or electrical connection. As such damage to buildings and/or infrastructure where the monitored environment is may be avoided.

The casing may be concave. The casing may be bowl-shaped. The casing may be a lower casing. The casing may take any suitable shape. The casing may conform to the shape of a portion of the sampling pipe. For example, the capsule may be flush with an outer surface of the sampling pipe when installed therein.

The portion may be planar. The portion may be a film. The portion may be an upper portion. The portion may be a heat sensitive upper lid or closure. The upper portion may form a lipped edge where it meets the casing. The portion may be take any shape as required. The portion may conform to at least a portion of the sampling pipe. For example, the capsule may be flush with an outer surface of the sampling pipe when installed therein.

The lower casing may be configured to collect the upper portion as it melts, ruptures or combusts when exposed to an environment at temperatures exceeding the predetermined threshold. The upper portion may undergo a phase change into a liquid state. The upper portion may become elastic upon melting. In this state, the upper portion may pool and/or collect in the lower casing.

Collecting the upper portion in the lower casing as the upper portion melts may prevent spillage of the upper portion. Collecting the upper portion in the lower casing may prevent the upper portion solidifying on and/or adhering to surfaces which it may otherwise damage e.g. the interior of the pipe. Residue from the portion may therefore be easily removed from the system by uninstalling the heat-detection device.

The capsule may be installed in the pipe in an orientation so that substantially only the airborne substance is emitted into the pipe. For example, the capsule may be installed in a bottom or lower surface of the sampling pipe. Other elements of the capsule e.g. the portion and/or the casing may not fall or pass into the sampling pipe. Blockage or reduction of flow through the sampling pipe may therefore be reduced or prevented.

The heat-detection device (e.g. capsule) may be easily replaced after emission of the airborne substance. Thus, it may be simpler and cheaper to reset the aspirating detection system described herein than known heat-detection systems (e.g. linear heat detection systems). It may also be feasible to detect lower temperature than with known heat-detection systems, since only a capsule needs to be replaced rather than e.g. an entire length of coated wiring.

Viewed from a second aspect, the invention provides a heat-detection capsule for use as the heat-detection device of the aspirating detection system of the first aspect of the invention.

The heat-detection capsule of the second aspect may therefore have one or more features corresponding to those of the heat-detection device of the first aspect of the invention. Thus the above description of the heat-detection device of the first aspect, including but not limited to all technical advantages and alternative embodiments, may be equally applicable to the heat-detection capsule of the second aspect.

Viewed from a third aspect, the invention provides a method of determining that a temperature in a monitored environment has exceeded a predetermined threshold, the method comprising: providing an aspirating detection system for aspirating and detecting an airborne substance; providing a substance or device arranged to emit the airborne substance when the temperature within the monitored environment exceeds the predetermined threshold; and determining in response to detection of the airborne substance that the temperature in the monitored environment has exceeded the predetermined threshold.

By using an aspirating detection system to detect heat rather than merely detecting smoke, it is possible to detect smokeless heat. This may allow for the detection of overheating events which may be indicative of e.g. damage to a monitored environment or its contents, and/or events which may be a precursor to such damage and/or a fire event.

The substance or device may be a heat-detection device. By providing a substance or device arranged to emit the airborne substance when the temperature within the monitored environment exceeds the predetermined threshold, the aspirating detection system may be able to detect when the monitored environment is subject to temperatures indicative of, for example, a fire. The aspirating detection system may be configured to detect the airborne substance rather than (or as well as) smoke. Smoke can be a result of for example a fire but also processes such as cooking or manufacturing that otherwise cause nuisance alarms. The heat-detection device may therefore indicate a fire by the emission of the airborne substance, rather than a generic smoke produced by a known source, and therefore the method may help reduce instances of false alarms.

As mentioned, the substance or device may emit the airborne substance in response to heat not necessarily from a fire source, but to any heat of the monitored environment which exceeds the predetermined threshold. By emitting the airborne substance when no airborne substance would otherwise be released, the substance or device may indicate heat conditions which suggest damage or future damage to, for example, electronic or machine components. The temperature may be a precursor to a fire. Preventative and/or failsafe measures may then be implemented such that damage to electronic or machine equipment, or otherwise, may be reduced, avoided and/or minimised.

Further, the substance or device may require no electronic components or wiring. That is, the heat-detection device may be a passive device. The heat-detection device may be suitable for installation in the aspirating detection system without electronic communication and/or electrical connection. As such damage to buildings and/or infrastructure may be avoided as no electronic wiring is necessary to provide adequate heat-detection. No wiring or electricity is needed for the aspirating detection system other than that required for the aspirating detector, which may (or may not) be located remotely from the environment to be monitored. The sampling pipe may be a plastic pipe or otherwise and may not require electronics. Accordingly no supplementary electronics or wires for electronic communication or currents are required in the monitored environment. Thus, the method may be performed without the provision of electricity in the monitored environment. It may therefore be employed for detecting heat in environments that cannot have electricity introduced therein.

The method may comprise raising an alarm in response to determining that that the temperature in the monitored environment has exceeded the predetermined threshold. The alarm may be a visual alarm and/or an aural alarm. The method may comprise generating the alarm by a siren, a speaker, a bell or the like. The method may comprise generating the alarm by a stroboscopic light, an LED or a display panel. The method may comprise generating a communication such as an email, SMS message or the like and sending the communication to a communication device such as a smartphone. The method may comprise cooling the monitored environment. The method may comprise releasing a suppressant into the monitored environment in order to reduce the temperature therein. Alternatively, the method may comprise not releasing a suppressant into the monitored environment in response to detecting that the temperature therein exceeds the predetermined threshold.

The method may comprise comparing the predetermined threshold to a temperature threshold, and the method may further comprise selecting a response based upon that comparison. For example, if the predetermined threshold is greater than the temperature threshold, the method may comprise responding differently than if the predetermined threshold is less than the temperature threshold. Thus, the method may be different depending on the absolute value of the predetermined threshold, since different temperatures may require different responses.

The method may comprise discharging a suppressant such as a fire suppressant in response to determining that that the temperature in the monitored environment has exceeded the predetermined threshold. The method may comprise cooling the environment in response to determining that the temperature in the monitored environment has exceeded the predetermined threshold, e.g. using an air-conditioning system or the like.

The method may comprise providing a fire panel and/or a command module. The method may comprise coordinating, in response to detecting the airborne substance and/or the determining that the temperature in the monitored environment has exceeded the predetermined threshold, a response of the aspirating detection system. The step of coordinating may be performed using the fire panel and/or command module. The step of raising an alarm may be performed using the fire panel and/or command module. The method may comprise generating a signal to cool the monitored environment using the fire panel and/or command module. The method may comprise generating a signal to discharge a suppressant into the monitored environment using the fire panel and/or command panel. The steps of generating a signal aforementioned may be performed in response to detecting the airborne substance and/or the determining that the temperature in the monitored environment has exceeded the predetermined threshold. The method may comprise sending a notification such as an email or a text message or the like in response to detecting that the temperature of the monitored environment exceeds the predetermined threshold. The notification may provide the predetermined threshold and indicate that the temperature exceeds that.

The method may comprise programming the fire panel to define a response of the aspirating detection system upon detecting the airborne substance and/or the determining that the temperature in the monitored environment has exceeded the predetermined threshold and/or command module.

The method may comprise detecting the airborne substance using an aspirating detector of the aspirating detection system.

The method may comprise installing the substance or device on and/or in a sampling pipe. The method may comprise installing the substance or device in an interior of the sampling pipe, or on an exterior of the sampling pipe. The method may comprise aspirating a sample of fluid e.g. air from the monitored environment via the sampling pipe. The method may comprise detecting smoke or the like in the aspirated sample.

The method may comprise configuring the aspirating detector to identify and/or distinguish between a plurality of airborne substances. The method may comprise identifying the airborne substance. The method may comprise distinguishing between a plurality of airborne substances. The plurality of airborne substances may be, e.g. smoke and the airborne substance emitted from the heat-detection device. These steps may be performed using the aspirating detector.

The method may comprise connecting the aspirating detector to a sampling pipe of the aspirating detection system. Thus the aspirating detection and the sampling pipe may be in fluid communication.

The method may comprise detecting the airborne substance using an optical sensing device.

The optical sensing device may be a nephelometer. The optical sensing device may comprise a laser head. The laser head may be a high sensitivity laser head.

The method may comprise detecting only the airborne substance.

The method may comprise aspirating a sample of air into the aspirating detection system through the sampling pipe. This may be performed using an aspirating device. The aspirating device may be a pump, a fan, a compressor, or any suitable means for drawing a sample into the system. The aspirating device may be part of the aspirating detector.

The method may comprise providing the sampling pipe at least partially within the monitored environment. The sampling pipe may thereby be exposed to the monitored environment and to conditions within the monitored environment. The method may comprise arranging at least a portion of the sampling pipe in thermal equilibrium with the monitored environment.

The method may comprise providing the substance or device within the monitored environment, and thereby exposing the substance or device to conditions within the monitored environment. The substance or device may therefore be heated in the event that the temperature in the monitored environment increases. The method may comprise arranging the heat-detection device in thermal equilibrium with the monitored environment.

The method may comprise mechanically coupling the substance or device to the sampling pipe. The method may comprise mechanically coupling a heat-detection device to the sampling pipe, and the heat-detection device may be mechanically coupled using any suitable means. The method may include providing a mechanical coupling for coupling the heat-detection device to the sampling pipe. The mechanical coupling may comprise e.g. a screw, a clamp, a slot or any suitable mechanism.

The method may comprise arranging the substance or device to seal an opening in the sampling pipe to the monitored environment. The method may comprise providing an opening in the sampling pipe to the monitored environment. The method may comprise sealing the sampling pipe using the device e.g. blocking the opening using a heat-detection device. The substance or device may thereby prevent fluid communication between the interior of the sampling pipe and the monitored environment, at least via the opening in the pipe at that location within the monitored environment. The substance or device may therefore prevent ingress into the sampling pipe from the monitored environment of smoke, particulates, or other substances that could be detected by the aspirating detector but which do not warrant an alarm. For example, if the monitored environment comprises a kitchen, a garage, and/or another environment in which smoke or the like is typically expected, the substance or device may function to prevent false alarms. The substance or device may adhere to the sampling pipe. In doing so the heat-detection device may be operable to seal the opening in the sampling pipe.

The heat-detection device and/or the sampling pipe may comprise a seal arranged to seal the heat-detection device in the opening of the sampling pipe.

The method may comprise providing a plurality of portions of the substance and/or the device. The interior of the sampling pipe may be entirely sealed (at least from the monitored environment) by that plurality of substances or devices. The aspirating detection system may therefore be configured to function as only a heat-detection system.

Alternatively, the substance(s) or device(s) may seal the sampling pipe only in a particular region of the monitored environment. For example, if the system is arranged to monitor a plurality of locations (e.g. including a kitchen and a library), the sampling pipe may be sealed by the heat-detection device(s) in one location (e.g. in the kitchen) to reduce the chance of false alarms from an environment where smoke or the like is expected, but may comprise openings in another location (e.g. in the library) for aspirating air and thereby detecting smoke in line with usual practices for an aspirating detection system. The method may comprise operating the aspirating detection system as both a typical aspirating detection system for detecting e.g. smoke, and a heat-detection system for detecting heat.

The method may comprise providing the substance or device within a juncture of the sampling pipe.

The monitored environment may comprise a first volume and a second volume. The sampling pipe may be provided at least partially in the first volume and at least partially in the second volume. The method may also include providing the substance or device in the first volume. The method may comprise providing an opening into the second volume in the sampling pipe for aspirating air from the second volume.

The second volume may be separate or substantially separate from the first volume. For example, the first volume may be one in which smoke or the like is typically expected (e.g. a kitchen), and the second volume may be one in which smoke is not typically expected (e.g. a library). The use of the substance or device as described herein may therefore enable the system to monitor different types of environment simultaneously.

It will be appreciated that although the same pipe may be partially disposed in the two volumes, the method may include providing a second sampling pipe for monitoring the second volume. The sampling pipe may therefore be a first sampling pipe and may be exposed at least partially to the first volume. The second sampling pipe may be exposed at least partially to the second volume. Any suitable number of pipes may be provided, and the monitored environment may comprise any suitable number of volumes, each volume monitored by at least one pipe.

The first volume may refer to a building, room and/or apparatus present in the monitored environment. The second volume may refer to a building, room and/or apparatus present in the monitored environment.

The monitored environment may comprise a plurality of volumes. Each volume may be substantially separated from the others. The method may comprise at least partially exposing the sampling pipe to each volume. The method may comprise providing a plurality of sampling pipes, and at least partially exposing the one or more sampling pipes to each volume. Thus, each volume may be served by at least one sampling pipe. The method may comprise installing one or more substances or devices in each sampling pipe. One or more of the sampling pipes may not have a substance or device installed. The method may comprise simultaneously monitoring a plurality of separate volumes.

The monitored environment may be the plenum of an apparatus. The first and/or second volume may be the plenum of an apparatus. The apparatus may be machinery. The apparatus may be an electrical apparatus. The apparatus may include, for example, a computer server. The plenum may be an empty space provided for cooling purposes and/or for housing various components. The plenum may be in fluid communication with the sampling pipe directly. The plenum may be in fluid communication with the sampling pipe indirectly, for example via a capillary tube e.g. for drawing fluid from the plenum into the sampling pipe.

By monitoring the apparatus including machinery and electrical apparatus, such devices may be monitored for overheating. Appropriate action may be taken to then preserve the condition of the apparatus or perform maintenance on the apparatus, for example. Such overheating events may be a precursor to fire events, or may just be likely to cause damage to the apparatus. Accordingly the method may determine if a monitored environment of an apparatus exceeds a given temperature.

The substance or device may be a first substance or device and the airborne substance may be a first airborne substance. The method may further include providing a second substance or device arranged to emit a second airborne substance when the temperature of the monitored environment exceeds a second predetermined threshold. The aspirating detection system may be for aspirating and detecting the first airborne substance and/or the second airborne substance. The step of determining may be in response to detection of the first airborne substance and/or the second airborne substance.

By providing a first substance or device and a second substance or device, each emitting a first and second airborne substance respectively when the temperature exceeds a predetermined threshold, the method may involve monitoring multiple locations within the environment, and may involve detecting when the temperature of the monitored environment at multiple locations exceeds the predetermined threshold.

The method may comprise determining a location within the monitored environment at which the temperature has exceeded the predetermined threshold, since the location of the substance or device (e.g. a heat-detection device) may be known. The method may comprise providing a notification indicating the determined location.

Further, the first substance or device may be different to the second substance or device. The method may involve distinguishing between the first substance or device and the second substance or device. The method may therefore involve identifying which substance(s) or device(s) was compromised. That is, which of the first and second substances or devices emitted its airborne substance upon being exposed to a temperature exceeding the predetermined threshold. An alarm may be raised, or further information deduced, based on which of the airborne substances was detected.

The first airborne substance and the second airborne substance may be different. The method may comprise arranging the first and second substances or devices to emit their respective airborne substances at the first and second predetermined thresholds respectively. The step of determining may include distinguishing between the first airborne substance and the second airborne substance. The method may therefore be able to distinguish which substance or device has been activated, and hence which predetermined threshold of temperature has been reached.

The method may include arranging the second substance or device to emit the second airborne substance when the temperature of the monitored environment exceeds a second predetermined threshold. The method may include arranging the first substance or device in the first volume and arranging the second substance or device in the second volume. The method may include determining which volume has a temperature in excess of the corresponding predetermined threshold. The method may include generating an alarm signal indicating heat-detection in the relevant volume may then be raised or any suitable action may be taken. The method may comprise providing a plurality of substances or devices, each with respective airborne substances and arranging the plurality of substances or devices to discharge those airborne substances when exposed to environments in excess of respective predetermined thresholds.

Although the first and second predetermined thresholds may be the same, they may also be different. The method may comprise positioning a first heat-detection device within a first volume and positioning a second heat-detection device within a second volume. The method may include detecting an increasing series of temperatures by detecting the first airborne substance, then detecting the second airborne substance. The method may include providing a notification in response to detecting the first airborne substance, and may further include cooling the monitored environment in response to detecting the second airborne substance. The first and second heat-detection devices may be provided in the same volume, and the method may therefore track progression of temperatures in that volume by sequential detection of the first and second airborne substances.

By being able to distinguish different temperatures in different volumes, the method may be able to provide bespoke heat-detection and determination. The combination of multiple substances or devices within a single aspiration detection may negate the need for multiple linear heat-detection systems to be installed.

The provided aspirating detection system may be a pre-existing and/or a preinstalled aspirating detection system. The providing of the substance or device may be a retrofitting of the substance or device to the aspirating detection system.

By retrofitting the aspirating detection system with the substance or device, existing aspirating detection systems may be repurposed for detecting heat exceeding a predetermined threshold via the airborne substance, the airborne substance emitted from the substance or device when exposed to temperatures exceeding the predetermined threshold. Retrofitting aspirating detection systems may save costs, as conventional linear heat detectors need not be installed alongside and/or in place of existing aspirating detection systems.

The method may comprise applying the substance to the sampling pipe e.g. in an interior of the sampling tube. The substance may be a heat-responsive and/or thermal paste. Upon exposure to the temperature exceeding the predetermined threshold, the substance may undergo a reaction and/or phase change which results in the emission of the airborne substance.

The provided device may be a heat-detection device. The heat-detection device may be the heat-detection device of the first or second aspect. The method may comprise installing the heat-detection device externally to the sampling pipe, or internally to the sampling pipe. The method may comprise installing the heat-detection device on an extension of the sampling pipe e.g. on or in a dedicated portion of the sampling pipe.

The use of the heat-detection device may have one or more features corresponding to use of the features of the first and second aspects. Thus the above description of the heat-detection device of the first and second aspects, including but not limited to all technical advantages and alternative embodiments, may be equally applicable to the method of the third aspect accordingly.

The heat-detection device may be a heat-detection capsule. The method may include arranging a portion of the heat capsule to structurally fail when the temperature of the monitored environment exceeds the predetermined threshold and thereby release the airborne substance.

The method may include enclosing the airborne substance, or a material emitting the airborne substance, using the portion and a casing. The airborne substance, or corresponding material, may be encapsulated and/or enclosed in an enclosure defined by the heat sensitive portion and the casing.

The method may include melting the portion when exposed to temperatures exceeding the predetermined threshold. The method may include forming the portion of a material with a melting point equal to the predetermined threshold, or less than the predetermined threshold. The method may include forming the portion of a polycarbonate material.

The method may include forming the casing. The casing may be formed of a heat resistant material. The casing may be formed of a heat stable material. The casing may be formed of polycarbonate acrylonitrile butadiene styrene (PC-ABS).

The casing may be a lower casing. The portion may be an upper portion.

The method may include collecting the upper portion in the lower casing as the upper portion melts may prevent spillage of the upper portion. Collecting the upper portion in the lower casing may prevent the upper portion solidifying on and/or adhering to surfaces which it may otherwise damage e.g. the interior of the pipe.

The method may comprise installing the capsule in the sampling pipe in an orientation so that substantially only the airborne substance is emitted into the pipe. For example, the capsule may be installed in a bottom or lower surface of the sampling pipe. Other elements of the capsule e.g. the portion and/or the casing may not fall or pass into the sampling pipe. Blockage or reduction of flow through the sampling pipe may therefore be reduced or prevented.

The method may comprise using the aspirating detection system of the first aspect and/or the heat-detection capsule of the second aspect. The device may be the heat-detection device of the first aspect and/or the heat-detection capsule of the second aspect. The provided aspirating detection system may be the aspirating detection system of the first aspect. The method may be a method of using the aspirating detection system of the first aspect for determining that a temperature in a monitored environment has exceeded a predetermined threshold.

The method may include discharging the airborne substance into a sampling pipe of the aspirating detection system. The method may include replacing a heat-detection device in the aspirating detection system after the airborne substance has been discharged from the heat-detection device.

The method of the third aspect may have one or more steps corresponding to the use and/or provision of features of the first and/or second aspects of the invention. Thus the above description of the systems and/or apparatus of the first and second aspects of the invention, including but not limited to all technical advantages and alternative embodiments, may be equally applicable to the method of the fourth aspect.

Viewed from a another aspect, the invention provides a method of assembling an aspirating detection system, the method comprising: providing an aspirating detector for aspirating and detecting smoke in a sample of air; providing a sampling pipe for providing a sample of air to the aspirating detector, the sampling pipe at least partially exposed to the monitored environment; and providing a heat-detection device exposed to the monitored environment and arranged to emit an airborne substance into the sampling pipe when the temperature of the monitored environment exceeds a predetermined threshold; wherein the aspirating detector is arranged to detect the airborne substance and thereby detect that the temperature of the monitored environment exceeds the predetermined threshold.

The aspirating detection system may be the aspirating detection system of the first aspect. Accordingly the method may be a method of assembling the aspirating detection system of the first aspect.

The method of this aspect may have one or more steps corresponding to the use of features of the first aspect. Thus the above description of the system of the first aspect, including by not limited to all technical advantages and alternative embodiments, may be equally applicable to the method of this aspect.

The method may include providing the sampling pipe at least partially within the monitored environment.

The method may include installing the heat-detection device on and/or in the sampling pipe.

The method may include mechanically coupling the heat-detection device to the sampling pipe.

The method may include arranging the heat-detection device to seal an opening in the sampling pipe to the monitored environment.

The method may include providing a plurality of heat-detection devices. The method may include arranging the plurality of heat-detection devices to entirely seal the interior of the sampling pipe from the monitored environment.

The method may include providing the sampling pipe at least partially within a first volume and at least partially within a second volume of the monitored environment. The method may include providing the heat-detection device in the first volume.

The method may include providing a first heat-detection device and providing a second heat-detection device. The method may include arranging the first heat-detection device in the first volume, and arranging he second heat-detection device in the second volume.

The method may include retrofitting the heat-detection device. The method may include retrofitting the heat-detection device in and/or on the sampling pipe.

Viewed from another aspect, the invention provides a heat-detection device exposed to a monitored environment and arranged to emit an airborne substance when the temperature of the monitored environment exceeds a predetermined threshold. The heat-detection device of this aspect may suitable for use as the heat-detection device described with reference to the first aspect of the invention. The heat-detection device of this aspect may therefore have one or more features corresponding to those of the first aspect. Thus the above description of the heat-detection device of the first aspect, including but not limited to all technical advantages and alternative embodiments, may be equally applicable to the heat-detection device of this aspect.

Viewed from another aspect the invention may provide a kit comprising a plurality of heat-detection devices. Each of the heat-detection devices may be configured to emit an airborne substance into a monitored environment when a temperature of the monitored environment exceeds a predetermined threshold.

The plurality of heat-detection devices may be a plurality of heat-detection devices for use as the heat detection devices of the first or second aspects of the invention.

The kit may be a kit for retrofitting at least one heat-detection device to an aspirating detection system, wherein the at least one heat-detection device is selected from the plurality of heat-detection devices.

By retrofitting an existing aspirating detection system with at least one heat-detection device, existing aspirating detection systems may be repurposed for detecting heat exceeding a predetermined threshold via the airborne substance, the airborne substance emitted from the heat-detection device when exposed to temperatures exceeding the predetermined threshold. Retrofitting aspirating detection systems may save costs, as conventional linear heat detectors need not be installed alongside and/or in place of existing aspirating detection systems.

In retrofitting existing aspirating detection systems, the aspirating detection system may be reconfigured to detect the airborne substance and thus heat exceeding the predetermined threshold. Retrofitting existing aspirating detection systems may therefore repurpose them such that additional detecting systems are not necessary for detecting heat.

The at least one heat-detection device may be retrofitted in and/or on a sampling pipe of the aspirating detection system.

The kit may also be a kit for replacing a heat-detection device in an aspirating heat-detection system, wherein the heat-detection device is selected from the plurality of heat-detection devices. For example, the emission of the airborne substance may only occur on the first instance the heat-detection device is exposed to temperatures exceeding the predetermined threshold.

By being able to replace only used heat-detection devices, rather than an entire heat-detection system, as with say a linear heat-detection system, costs may be reduced. Additionally or alternatively, damage to the monitored environment may be reduced, as maintenance may only be required where the heat-detection device is located.

Viewed from another aspect, the invention provides an aspirating detection system configured to detect heat. The system may comprise a heat-detecting device. The system may comprise any of the features of the aspirating systems described herein with reference to the any of the aspects.

Viewed from another aspect, the invention provides a method of using an aspirating detection system to detect heat. The method may comprise providing a dedicated, heat-responsive component. The method may comprise any of the features of the methods described herewith with reference to any of the aspects.

DRAWING DESCRIPTION

Certain exemplary embodiments of the invention are described below by way of example only and with reference to the accompanying drawings in which.

DETAILED DESCRIPTION

Figure 1:
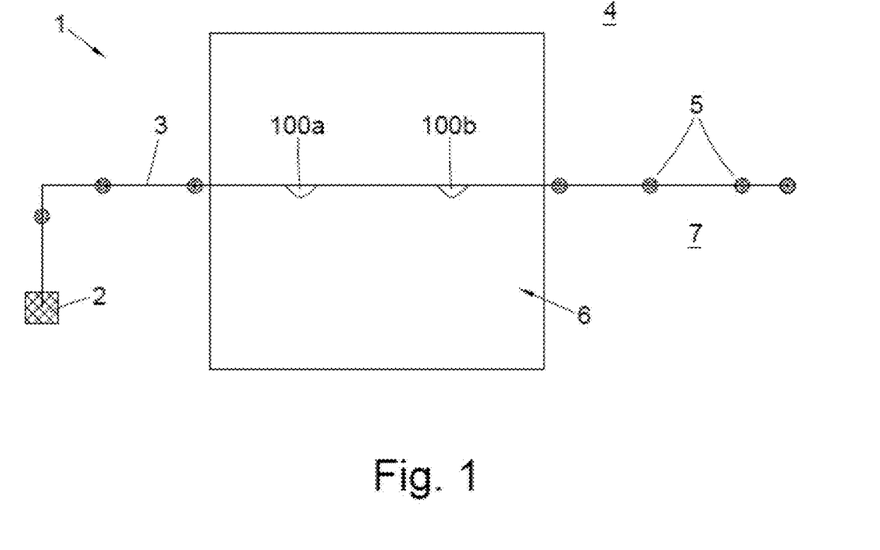
FIG. 1 shows an aspirating detection system.
Figure 2:
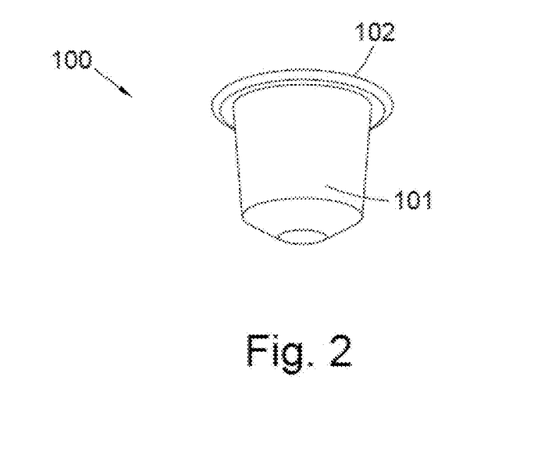
FIG. 2 shows a heat-detection device.

FIG. 1 shows an aspirating detection system 1. The aspirating detection system 1 comprises an aspirating detector 2 and a sampling pipe 3. The sampling pipe 3 is in fluid communication with the aspirating detector 2, and is configured to facilitate a flow of aspirated air to the aspirating detector 2. The aspirating detector 2 may aspirate air using an aspirating device (not shown). The aspirating device may be a pump, fan, blower, compressor or the like. The aspirating device can be a component of the aspirating detector 2, or may be a separate element of the system 1. The aspirating detector 2 may then detect an airborne substance in the aspirated air. Aspirating detection systems may be used for the detection of smoke, natural gas, carbon monoxide and other airborne substances and/or gases.

The aspirating detection system 1 monitors an environment 4 comprising a first volume 6 and a second volume 7. The aspirated air is aspirated from the monitored environment 4 (e.g. from the second volume 7) and thus the aspirated air may therefore be regarded as a sample of the air of the second volume 7 of the monitored environment 4. To aspirate the air, the sampling pipe 3 is disposed at least partially in the monitored environment 4. A number of openings 5 are present in the sampling pipe 3 such that the aspirating detector 2 is in fluid communication with the monitored environment 4. As can be seen in FIG. 1, the aspirating detector 2 need not necessarily be placed in the monitored environment 4, due to the sampling pipe 3 connecting the two. However, the aspirating detector could be located in the monitored environment 4.

A number of openings 5 may be present in the sampling pipe 3. The sampling pipe 3 is typically a simple plastic pipe, and the openings 5 are typically drilled into the pipe to provide fluid communication from the environment 4 to the aspirating detector. In the depicted system 1 in FIG. 1, the openings 5 are outside of first volume 6 of the monitored environment 4. As such the aspirating detection system 1 can monitor multiple volumes of the environment 4 e.g. the first volume 6 and second volume 7.

The aspirating detector 2 may be configured to detect, for example, smoke. The smoke may be the result of combustion from known sources such as cooking sources or manufacturing processes. Similarly the smoke could be produced from fire sources which are not known and may therefore pose a serious safety risk or danger. However, without being able to distinguish between smoke produced from a known or an unknown source, smoke produced by known sources may result in nuisance alarms.

The first volume 6 of the monitored environment 4 could be e.g. a kitchen, factory, or other volume of the environment 4 where smoke from known sources is prevalent. As such, instead of openings in the sampling pipe 3 into the first volume 6, heat-detection devices 100a, 100b are provided installed in and/or on the sampling pipe 3 of the aspirating detection system 1. Thus, smoke or other particulates are prevented from entering the sampling pipe 3 in this volume.

The heat-detection devices 100a, 100b are responsive to heat, rather than smoke. When exposed to an atmosphere at a predetermined threshold temperature, a heat-detection device 100a, 100b emits an airborne substance into the sampling pipe 3, which airborne substance is detectable by the aspirating detector 2. Thus, the aspirating detector 2 will receive a signal when the first volume 6 is at the predetermined threshold temperature. Whilst two heat-detection devices 100a, 100b are provided in the shown aspirating detection system 1, one or more heat-detection devices 100 may be provided as required.

Each heat-detection device 100 may seal a corresponding opening 5 in the portion of the sampling pipe 3 which is partially disposed in the first volume 6 of the monitored environment 4. As such smoke may be prevented from being aspirated from the first volume 6 to the aspirating detector 2 and causing nuisance alarms. Any suitable sealing may be provided, and the heat-detection device 100 may block an opening in the sampling pipe 3. Thus, the heat-detection device 100 may help prevent false alarms.

Instead, the heat-detection device 100 emits an airborne substance into the sampling pipe 3 when the temperature of the first volume 6 of the monitored environment 4 exceeds a predetermined threshold. The predetermined threshold may be regarded as the temperature which is to be detected by the system 1. The airborne substance is aspirated to the aspirating detector 2 through the sampling pipe 3, where it is detected. By detecting the airborne substance, the aspirating detector 2 is able to indirectly detect heat at a temperature which exceeds the predetermined threshold.

The aspirating detector 2 may be configured to detect only the airborne substance, or may detect the airborne substance and smoke etc. However, the smoke may be from other volumes of the environment 4 only due to the sealing of the openings 5 in the smoky first volume 6 of the monitored environment 4.

Alternatively, the aspirating detector 2 may be configured to detect a first airborne substance of a first heat-detection device 100a configured to emit the first airborne substance at a first predetermined temperature, and also configured to detect a second airborne substance of a second heat-detection device 100b configured to emit the second airborne substance at a second predetermined temperature. The aspirating detector 2 may be able to identify and distinguish between the first and second airborne substances.

If the first heat-detection device 100a is located in the first volume 6 of the monitored environment 4, and the second heat-detection device 100b is located in another volume (not shown) of the monitored environment 4, the emission and subsequent detection of the first and/or second airborne substance will allow the aspirating detector 2 to be able to determine when the first and/or the second predetermined threshold for heat is/are reached in each volume 6, 7 of the environment 4. Accordingly the aspirating detection system 1 may be able to monitor heat in multiple environments, and determine which of a plurality of volumes has reached the predetermined threshold.

Additionally and/or alternatively the first predetermined temperature may differ to the second predetermined temperature. As such varying heat detection requirements may be fulfilled across multiple volumes 6, 7 of the environment 4. For example, as shown in FIG. 1, the first heat-detection device 100*a* may emit the first airborne substance when the first volume 6 reaches a first predetermined threshold temperature. The second heat-detection device 100*b* may emit the second airborne substance when the first volume 6 reaches a second predetermined threshold temperature. The aspirating detector 2 can detect and distinguish between the first and second airborne substances and hence can monitor temperature progression within the first volume 6.

Moreover, since the heat-detection process of the system 1 relies only upon a single heat-detection device 100 (e.g. a heat-detection capsule) which is readily replaceable, it is feasible (practically and financially) to use the system 1 to detect lower temperatures than would be done with known (e.g. linear) heat detection systems. That is, it is simple to replace a heat detection device 100*a*, 100*b* in the event that it is activated to emit its airborne substance. The system 1 can therefore easily be reset, which stands in contrast to known linear heat detection systems that need e.g. replacement of an entire installed, coated wire pair. The system 1 may therefore be used to provide an early warning, raising an alarm or taking action at temperatures that are merely pre-cursors to safety critical events, rather than themselves being safety critical events per se.

All the while, monitoring of the second volume 7 can be maintained in the usual manner, since the aspirating detector 2 can also detect smoke or the like aspirated from the second volume 7 via the openings 5 in the sampling pipe 3. Thus, functionality of the aspirating detection system 1 is increased compared to known systems.

Turning to FIG. 2, a heat-detection device 100 is shown. The heat-detection device 100 shown in FIG. 2 may be regarded as a heat-detection capsule. The heat-detection device 100 comprises a casing 101 and a closure 102. The closure 102 may also be regarded as a lid 102. The closure 102 is a portion of the heat-detection device 100 which is designed to structurally fail (and thereby open the capsule) when exposed to temperatures exceeding the predetermined threshold, and hence release the airborne substance. For the shown heat-detection device 100, the closure 102 could melt, combust or rupture when exposed to such temperatures. A material emitting the airborne substance, or the airborne substance itself, which was previously enclosed and/or encapsulated in the heat-detection device 100, may then be in fluid communication with the sampling pipe 3, and as such the airborne substance can be aspirated to the aspirating detector 2, where it is detected.

The heat-detection device 100 can take any suitable form. In the depicted example, it is a capsule 100 that is installed on the sampling pipe 3 with the lid 102 oriented into an opening 5. The capsule 100 may be adhered (e.g. with glue) to the sampling pipe 3 in the appropriate location, or it may be mechanically coupled e.g. using a screw arrangement, a bayonet, a slot and so on. Thus, it may be simple to retro-fit a known aspirating detection system, and/or to re-set the system 1 as described herein following a detection event (i.e. following emission of an airborne substance by a heat-detection capsule 100). The heat-detection device 100 may be single-use, and may require replacement after a detection event.

The heat which the heat-detection device 100 is exposed to and/or detects need not necessarily be from a fire, and can also be a smokeless heat. Accordingly the aspirating detector 2 can not only detect heat events producing smoke, but other heat events such as the overheating of apparatus, for example electrical equipment or machinery, in the monitored environment.

What is claimed is:

1. An aspirating detection system for monitoring an environment, the system comprising:

an aspirating detector for aspirating and detecting smoke in a sample of air;

a sampling pipe for providing a sample of air to the aspirating detector, the sampling pipe at least partially exposed to the monitored environment; and a heat-detection device exposed to the monitored environment and arranged to emit an airborne substance into the sampling pipe when the temperature of the monitored environment exceeds a predetermined threshold;

wherein the aspirating detector is arranged to detect the airborne substance and thereby detect that the temperature of the monitored environment exceeds the predetermined threshold; and wherein the heat-detection device is arranged to seal an opening in the sampling pipe to the monitored environment such that only the airborne substance is emitted via the opening into the sampling pipe for detection by the aspirating detector when the temperature of the monitored environment exceeds the predetermined threshold.

2. An aspirating detection system as claimed in claim 1, wherein the heat-detection device is installed on the sampling pipe.

3. An aspirating detection system as claimed in claim 1, wherein the airborne substance is at least one of an aerosol or a target gas.

4. An aspirating detection system as claimed in claim 3, wherein the airborne substance is paraffin smoke.

5. An aspirating detection system as claimed in claim 1, wherein the monitored environment comprises a first volume and a second volume;

wherein the sampling pipe is disposed at least partially in the first volume and at least partially in the second volume;

wherein the heat-detection device is disposed in the first volume; and wherein the sampling pipe comprises an opening into the second volume for aspirating air from the second volume.

6. An aspirating detection system as claimed in claim 1, wherein the heat-detection device is a first heat-detection device and the airborne substance is a first airborne substance, the system further comprising:

a second heat-detection device arranged to emit a second airborne substance when the temperature of the monitored environment exceeds a second predetermined threshold;

wherein the aspirating detector is operable to detect the second airborne substance; and wherein the first airborne substance is different from the second airborne substance.

7. An aspirating detection system as claimed in claim 1, wherein the heat-detection device is a heat-detection capsule comprising a portion arranged to structurally fail when the temperature of the monitored environment exceeds the predetermined threshold and thereby release the airborne substance.

8. An aspirating detection system as claimed in claim 7, wherein the heat-detection capsule further comprises a casing;
   wherein the casing and the portion are arranged to encapsulate the airborne substance.

9. An aspirating detection system as claimed in claim 7, wherein the portion is formed of a polycarbonate material.

10. An aspirating detection system as claimed in claim 7, wherein the portion is configured to melt when the temperature of the monitored environment exceeds the predetermined threshold.

11. An aspirating detection system as claimed in claim 1, wherein the heat-detection device is a heat-detection capsule.

12. An aspirating detection system as claimed in claim 1, wherein the heat-detection device is a first heat-detection device and the airborne substance is a first airborne substance, the system further comprising:
   a second heat-detection device arranged to emit a second airborne substance when the temperature of the monitored environment exceeds a second predetermined threshold;
   wherein the aspirating detector is operable to detect the second airborne substance; and
   wherein the first airborne substance is the same as the second airborne substance.

13. An aspirating detection system as claimed in claim 1, wherein the heat-detection device is installed in the sampling pipe.

14. A method of determining that a temperature in a monitored environment has exceeded a predetermined threshold, the method comprising:
   providing an aspirating detection system for aspirating and detecting an airborne substance;
   arranging a substance or device to seal an opening in a sampling pipe of the aspirating detection system, wherein the substance or device is arranged to emit the airborne substance when the temperature within the monitored environment exceeds the predetermined threshold, and wherein the substance or device is arranged such that only the airborne substance is emitted into the sampling pipe above the predetermined temperature for detection by the aspirating detection system when the temperature of the monitored environment exceeds the predetermined threshold; and
   determining in response to the detection of the airborne substance that the temperature in the monitored environment has exceeded the predetermined threshold.

15. A method as claimed in claim 14, the method comprising:
   determining the location of the temperature exceeding the predetermined threshold based on the type of airborne substance detected.

16. A method as claimed in claim 14, the method comprising:
   retrofitting the substance or device to the aspirating detection system.

* * * * *